US007119217B2

(12) United States Patent
Jiang et al.

(10) Patent No.: US 7,119,217 B2
(45) Date of Patent: Oct. 10, 2006

(54) TRI(ALKYLCARBOXYLATO)GALLIUM (III) PRODUCTS AND PHARMACEUTICAL COMPOSITIONS CONTAINING THEM

(75) Inventors: Jack B. Jiang, Orange Village, OH (US); Raymond P. Warrell, Jr., Westfield, NJ (US); Kollengode K. Ramaswamy, Farmington, CT (US); Robert E. Klem, Rancho Santa Fe, CA (US)

(73) Assignee: Genta Incorporated, Berkeley Heights, NJ (US)

( * ) Notice: Subject to any disclaimer, the term of this patent is extended or adjusted under 35 U.S.C. 154(b) by 260 days.

(21) Appl. No.: 10/668,473

(22) Filed: Sep. 22, 2003

(65) Prior Publication Data

US 2005/0261366 A1 Nov. 24, 2005

Related U.S. Application Data

(60) Provisional application No. 60/412,986, filed on Sep. 23, 2002.

(51) Int. Cl.
*C07F 5/00* (2006.01)
*A61K 33/24* (2006.01)
*A61K 31/28* (2006.01)

(52) U.S. Cl. ............... 556/1; 514/492; 424/650
(58) Field of Classification Search ............ 556/1; 514/492; 424/650
See application file for complete search history.

(56) References Cited

U.S. PATENT DOCUMENTS

| | | | | |
|---|---|---|---|---|
| 4,529,593 | A | 7/1985 | Warrell, Jr. et al. | 424/127 |
| 5,175,006 | A * | 12/1992 | Matkovic et al. | 424/650 |
| 5,177,068 | A | 1/1993 | Callingham et al. | 514/184 |
| 5,258,376 | A | 11/1993 | Bernstein | 514/184 |
| 5,281,578 | A * | 1/1994 | Bradley et al. | 514/6 |
| 5,574,027 | A | 11/1996 | Bernstein | 514/184 |
| 5,747,482 | A | 5/1998 | Bernstein | 514/184 |
| 5,883,088 | A | 3/1999 | Bernstein | 514/184 |
| 5,968,922 | A | 10/1999 | Bernstein | 514/184 |
| 5,981,518 | A | 11/1999 | Bernstein | 514/184 |
| 5,998,397 | A | 12/1999 | Bernstein | 514/184 |
| 6,004,951 | A | 12/1999 | Bernstein | 514/184 |
| 6,048,851 | A | 4/2000 | Bernstein | 514/184 |
| 6,087,354 | A | 7/2000 | Bernstein | 514/184 |
| 6,656,615 | B1 | 12/2003 | Dwilinski et al. | 428/698 |
| 2005/0220895 | A1* | 10/2005 | Bucalo et al. | 424/617 |

FOREIGN PATENT DOCUMENTS

EP 0 502 709 A2 * 9/1992

OTHER PUBLICATIONS

Hart et al., "Antitumor Activity and Toxicity of Salts of Inorganic Group IIIa Metals: Aluminum, Gallium, Indium, and Thallium," Proc. Natl. Acad. Sci USA, vol. 68, No. 7 (Jul. 1971) pp. 1623-1626.
D.J. Straus, "Gallium Nitrate in the Treatment of Lymphoma," Seminars in Oncology, vol. 30, No. 2, Suppl. 5 (Apr. 2003) pp. 25-33.
E.A. Van Leeuwen-Stok et al., "Cell Cycle Dependency of [67] Gallium Uptake and Cytotoxicity in Human Cell Lines of Hematological Malignancies," Leukemia and Lymphoma, vol. 31(5-6) (Nov. 1998) pp. 533-544.
R.P. Warrell, Jr. et al., "Salvage Chemotherapy of Advanced Lymphoma with Investigational Drugs: Mitoguazone, Gallium Nitrate, and Etoposide [1,2]," Cancer Treatment Response, vol. 71, No. 1 (Jan. 1987) pp. 47-51.
M.S. Myette et al., "Interaction of gallium nitrate with other inhibitors of ribonucleotide reductase: effects on the proliferation of human leukemic cells," Cancer Letters, vol. 129, No. 2 (Jul. 17, 1998) pp. 199-204.
C.R. Chitambar et al., "Evaluation of Continuous-Infusion Gallium Nitrate and Hydroxyurea in Combination for the Treatment of Refractory Non-Hodgkin's Lymphoma," Am. J. Clin. Oncol., vol. 20, No. 2 (Apr. 1997) pp. 173-178.
R.P. Warrell et al., "Gallium Nitrate Inhibits Calcium Resorption from Bone and is Effective Treatment for Cancer-related Hypercalcemia," J. Clin. Invest., vol. 73 (May 1984) pp. 1487-1490.
R.P. Warrell, Jr. et al., "Gallium Nitrate for Preservation of Bone Mass in Multiple Myeloma: Results of a Pilot Randomized Study," Journal of Bone and Mineral Research, vol. 5 (Suppl. 2) (Aug. 28, 1990) pp. S106.
R.P. Warrell, Jr. et al., "Low-Dose Gallium Nitrate for Prevention of Osteolysis in Myeloma: Results of a Pilot Randomized Study," Journal of Clinical Oncology, vol. 11, No. 12 (Dec. 1993) pp. 2443-2450.
R.P. Warrell, Jr., "Gallium Nitrate for the Treatment of Bone Metastases," Cancer, vol. 80, No. 8 (Oct. 15, 1997) pp. 1680-1685.
C.R. Chitambar, "Gallium Nitrate Revisited," Seminars in Oncology, vol. 30, No. 2, Suppl. 5 (Apr. 2003) pp. 1-4.
R.P. Warrell, Jr. et al., "Gallium Nitrate for Advanced Paget Disease of Bone: Effectiveness and Dose-REsponse Analysis," Annals of Internal Medicine, vol. 113, No. 11 (Dec. 1990) pp. 847-851.
R. Bockman, "The Effects of Gallium Nitrate on Bone Resorption," Seminars in Oncology, vol. 30, No. 2, Suppl.5 (Apr. 2003) pp. 5-12.
N. Makkonen et al., "The effect of free gallium and gallium in liposomes on cytokine and nitric oxide secretion from macrophage-like cells in vitro," Inflamm. Res., vol. 44, No. 12 (Dec. 1995) pp. 523-528.

(Continued)

*Primary Examiner*—Porfirio Nazario-Gonzalez
(74) *Attorney, Agent, or Firm*—Kenyon & Kenyon LLP

(57) ABSTRACT

Provided are novel tri(alkylcarboxylato) gallium (III) compounds, exemplified by tripalmitato gallium (III), methods for making them, pharmaceutical compositions containing them, and methods of using the pharmaceutical compositions.

58 Claims, No Drawings

OTHER PUBLICATIONS

G. Apseloff, "Therapeutic Uses of Gallium Nitrate: Past, Present, and Future," American Journal of Therapeutics, No. 6 (1999) pp. 327-339.

I.M. Viktorova et al., "Gallium and Indium Acylates," pp. 929-930; translated from Doklady Akademii Nauk SSSR, vol. 189, No. 3 (Nov. 1969) pp. 541-542.

H.C. Dudley et al., "Preparation and Properties of Gallium Lactate [1]," The Journal of the American Chemical Society, vol. 70 (Sep.-Dec. 1948) p. 3942-3943.

Per Artursson et al., "Caco-2-Monolayers in Experimental and Theoretical Predictions of Drug Transport," Advanced Drug Delivery Reviews, vol. 46 (2001) pp. 27-43.

Shiyin Yee, "In Vitro Permeability Acros Caco-2-Cells (Colonic) Can Predict in Vivo (Small Intestinal) Absorption in Man—Fact or Myth," Pharmaceutical Research, vol. 14, No. 6 (1997) pp. 763-766.

Edward Rudnic et al., "Oral Solid Dosage Forms," Chapter 92, *Remington: The Science and Practice of Pharmacy*, vol. II, Alfonso R. Gennaro, Ed., 1995, pp. 1615-1649.

\* cited by examiner

TRI(ALKYLCARBOXYLATO)GALLIUM (III) PRODUCTS AND PHARMACEUTICAL COMPOSITIONS CONTAINING THEM

RELATED APPLICATIONS

The present Application claims the benefit of the Sep. 23, 2002 filing date of U.S. Provisional Patent Application 60/412,986.

FIELD OF THE INVENTION

The present invention relates to products, denominated tri(alkylcarboxylato) gallium (III) products, that can be prepared from gallium salts and alkylcarboxylate compounds. The present invention further relates to pharmaceutical compositions and dosage forms thereof that contain gallium (III).

BACKGROUND

The use of gallium administered in a variety of gallium-containing compounds to treat mammalian and human disease is well known. Gallium was initially identified as an antineoplastic agent by Hart, et al. (*Proc Natl Acad Sci USA*, Vol. 68, 1971, pp. 1623–1626), and has subsequently been reported to be effective against a variety of cancers, including particularly hematological malignancies such as leukemias, lymphomas (e.g., non-Hodgkin's lymphoma), multiple myeloma and Hodgkin's Disease. See, e.g., D. J. Straus, *Semin Oncol* Vol. 30(2 Suppl 5), April 2003, pp. 25–33; E. A. Van Leeuwen-Stok, et al., *Leuk Lymphoma*, Vol. 31(5–6), November 1998, pp. 533–544; R. P. Warrell, et al., *Cancer Treat Rep*, Vol. 71, 1987, pp. 47–51; M. S. Myette, et al., *Cancer Lett*, Vol. 129(2), Jul. 17, 1998, pp. 199–204; C. R. Chitambar, et al., *Am J Clin Oncol*, Vol. 20(2), April 1997, pp. 173–178.

It has also been reported that gallium is a potent inhibitor of bone resorption, leading to its use to treat hypercalcemia associated with cancer (R. P. Warrell, et al., *J Clin Invest*, Vol. 73, May 1984, pp. 1487–1490) as well as other diseases characterized by accelerated bone loss, such as multiple myeloma (R. P. Warrell, et al., *J Bone Mineral Res*, Vol. 5 (Suppl 2), Aug. 28, 1990, pp. S106; R. P. Warrell, et al., *J Clin Oncol*, Vol. 11(12), December 1993, pp. 2443–2450), bone metastases (R. P. Warrell, *Cancer*, Vol. 80, 1997, pp. 1680–1685), hyperparathyroidism (U.S. Pat. No. 4,529,593; C. R. Chitambar, *Semin Oncol*, Vol. 30(2 Suppl 5), April 2003, pp. 1–4), Paget's disease (R. P. Warrell, et al., *Ann Int Med*, Vol. 113, 1990, pp. 847–851) and osteoporosis (U.S. Pat. No. 4,529,593; R. Bockman, *Semin Oncol* Vol. 30(2 Suppl 5), April 2003, pp. 5–12). The actions of gallium on bone are different from bisphosphonates, and appear to be mediated by inhibition of the ATPase-dependent proton pump of osteoclasts, which decreases acid secretion (R. Bockman, *Semin Oncol* Vol. 30(2 Suppl 5), April 2003, pp. 5–12).

Gallium is reported to accumulate at sites of inflammation and infection and has well-known immunosuppressive properties. Macrophages in particular accumulate gallium, presumably as a result of their ability to engulf protein-iron complexes, resulting in inhibition of the release of inflammatory mediators from the cells. See N. Makkonen, et al. *Inflamm Res*, Vol. 44(12), December 1995, pp. 523–528. Gallium has reported efficacy in animal models of autoimmune disease and hypersensitivity, including type 1 diabetes, experimental autoimmune encephalomyelitis, experimental pulmonary inflammation, cardiac allograft rejection, experimental autoimmune uveitis, endotoxic shock, and systemic lupus erythematosus (G. Apseloff, *Am J Ther*, Vol. 6(6), November 1999, pp. 327–339). Gallium, therefore, holds particular promise as a therapy for disorders involving the immune system, in particular autoimmune diseases and conditions or diseases involving a cell-mediated (e.g., macrophage-mediated) immune response.

As evidenced by the foregoing, the therapeutic utility of gallium as a component of a variety of compounds and complexes is established. The compounds of the present invention, therefore, will exhibit a similar range of therapeutic activities and utilities as described above. However, gallium compounds that are better tolerated and have better bioavailability are needed.

The use of gallium 3-hydroxy-4-pyrones (maltols), preferably administered orally, to treat gallium-susceptible conditions has been the subject of several United States. Patents, including U.S. Pat. Nos. 5,258,376; 5,574,027; 5,747,482; 5,883,088; 5,968,922; 5,981,518; 5,998,397; 6,004,951; 6,048,851; and 6,087,354 (to Bernstein). The gallium maltol complex is prepared by reacting a gallium salt, such as halide or nitrate, with a 3-hydroxy-4-pyrones in solution. The electrostatic neutral state of the 3:1 gallium maltol complex is reported by Bernstein to improve the bioavailability of the gallium when compared to the ionic gallium salts, such as gallium nitrate.

Gallium triacetate has been reported. However, to the best of our knowledge, use of such gallium compounds as pharmaceutical formulations has not been reported. To the best of our knowledge, other gallium alkyl carboxylate products, including gallium tripalmitate, have not been reported in the literature.

With respect to synthetic routes to prepare gallium tricarboxylates, it has been reported that no appreciable dissolution of the metallic gallium was observed upon refluxing gallium metal in either glacial acetic acid or propionic acid for up to ten days, and the desired gallium tricarboxylates were not produced. Reacting gallium oxide and acetic acid resulted in a low yield of an impure gallium triacetate. A preferred preparative route for gallium triacetate was reported to be an exchange reaction between thallium acetate and gallium trichloride. See I. M. Viktorova, *Doklady Akademii Nauk SSSR*, Vol. 189, No. 3, November 1969, pp. 541–42 (English translation).

A preparative route for the gallium-containing product, gallium trilactate, is disclosed by Dudley, et al. The synthetic process starts by reacting metallic gallium with hydrochloric and nitric acid, followed by precipitation of gallium hydroxide upon addition of ammonium hydroxide. The gallium hydroxide is, in turn, reacted with lactic acid to produce the trilactate gallium complex. See H. C. Dudley, R. G. Garzoli, *J Am. Chem. Soc.*, Vol. 70, (1948), p. 3942.

Thus, while the pharmaceutical use of the nitrate and maltol salts of gallium to treat numerous diseases and conditions has been reported, the literature does not appear to have identified a pharmaceutical compound composed of gallium tricarboxylate products with a carboxylate substituent of more than three carbons. Indeed, direct, high yield preparative routes starting with either metallic gallium or gallium salts, for even the smaller tricarboxylate complexes, have not been heretofore disclosed. What is needed, therefore, is a high yield preparative route for gallium tricarboxylates of four carbons and higher, for example, for subsequent use as pharmaceutical compounds.

SUMMARY OF THE INVENTION

In one aspect, the present invention relates to tri(alkylcarboxylato) gallium (III) products formed by the reaction of an alkyl carboxylate compound of structure $$[R\text{---}CO_2]_xM$$

wherein X is 1 or 2, R is a linear or branched alkyl group having from 2 to about 26 carbon atoms, especially 3 to about 26 carbon atoms, most especially 3, 5, 7, 9, 11, 13, 15, or 17 carbon atoms, and M is selected from the group consisting of hydrogen and the alkali metals when X is 1, and the alkaline earth metals when X is 2; with a gallium salt. A mixture of two or more alkyl carboxylate compounds having different "R" can also be used.

In another aspect, the present invention relates to tri (alkylcarboxylato) gallium (III) products formed by the reaction of an alkyl carboxylate compound, or a mixture of alkyl carboxylate compounds, of structure $$[R\text{---}CO_2]_xM$$

wherein X is 1 or 2, R is a linear or branched alkyl group having from 2 to about 26 carbon atoms, and M is selected from the group consisting of hydrogen and the alkali metals when X is 1, and the alkaline earth metals when X is 2; with a gallium salt selected from gallium acetate, gallium nitrate, and the gallium halides.

In another aspect, the present invention relates to tri (alkylcarboxylato) gallium (III) products formed by the reaction of an alkyl carboxylate compound of structure $$R\text{---}CO_2M$$

wherein R is a linear or branched alkyl group having from 2 to about 26 carbon atoms and M is hydrogen, with a gallium salt, especially gallium acetate, gallium nitrate, and the gallium halides, in the presence of an inorganic base, especially an alkali or alkaline earth metal carbonate or bicarbonate, or an alkali or alkaline earth metal hydroxide, especially in the presence of a solvent that includes an alkyl alcohol, especially methanol, ethanol, n-propanol, iso-propanol, n-butanol, 2-butanol, iso-butanol, or t-butanol. The solvent can also include water. A mixture of alkyl carboxylate compounds, e.g. selected from $RCO_2M$, $R'CO_2M$ and $R''CO_2M$, wherein R' and R'' are defined as R and R, R', and R'' can be the same or different, can also be used. In this case, a tri(alkylcarboxylato) gallium (III) product that can be represented by $[RCO_2][R'CO_2][R''CO_2]Ga$ can be obtained.

In another aspect, the present invention relates to tri (alkylcarboxylato) gallium (III) products formed by the reaction of an alkyl carboxylate compound, or mixture of compounds, of structure $$[R\text{---}CO_2]_xM$$

wherein X is 1 or 2, R is a linear or branched alkyl group having 3, 5, 7, 11, 13, 15, or 17 carbon atoms, and M is selected from the group consisting of hydrogen and the alkali metals when X is 1, and the alkaline earth metals when X is 2; with a gallium salt, especially gallium acetate, gallium nitrate, or a gallium halide, especially wherein the reaction is carried-out in the presence of a solvent that includes an alky alcohol, especially methanol, ethanol, n-propanol, iso-propanol, n-butanol, 2-butanol, iso-butanol, or t-butanol. The solvent can also include water.

In another aspect, the present invention relates to tri (alkylcarboxylato) gallium (III) products formed by the reaction of an alkyl carboxylate compound of structure $$[R\text{---}CO_2]_xM$$

wherein X is 1 or 2, R is a linear or branched alkyl group having from 2 to about 26 carbon atoms, and M is selected from the group consisting of hydrogen and the alkali metals when X is 1, and the alkaline earth metals when X is 2; with a gallium salt, especially gallium acetate, gallium nitrate, or a gallium halide, wherein the reaction is carried out in the presence of a solvent that includes an alkyl alcohol selected from methanol, ethanol, n-propanol, iso-propanol, 2-butanol, t-butanol, and iso-butanol. A mixture of alkyl carboxylate compounds can also be used.

In yet a further aspect, the present invention relates to tri(alkylcarboxylato) gallium (III) products formed by the reaction of an alkyl carboxylate compound, or mixture of alkyl carboxylate compounds, of structure $$[R\text{---}CO_2]_xM$$

wherein X is 1 or 2, R is a linear or branched alkyl group having 15 carbon atoms, and M is selected from the group consisting of hydrogen and the alkali metals when X is 1, and the alkaline earth metals when X is 2; with a gallium salt, especially gallium acetate, gallium nitrate, or a gallium halide.

In another aspect, the present invention relates to tri (alkylcarboxylato) gallium (III) products formed by the reaction, at reflux, of an alkyl carboxylate compound, or mixture of alkyl carboxylate compounds, of structure $$[R\text{---}CO_2]_xM$$

wherein X is 1 or 2, R is a linear or branched alkyl group having from 2 to about 26 carbon atoms, and M is selected from the group consisting of hydrogen and the alkali metals when X is 1, and the alkaline earth metals when X is 2; with a gallium salt, especially gallium acetate, gallium nitrate, or a gallium halide, wherein the reaction is carried out in the presence of a solvent that includes both an alkyl alcohol, especially methanol, ethanol, n-propanol, iso-propanol, 2-butanol, t-butanol, and iso-butanol, and water and wherein the pH is greater than about 8.

In another aspect, the present invention relates to tri (alkylcarboxylato) gallium (III) compounds having an alkyl carboxylate substituent, $RCO_2$—, wherein R has 2 to about 26 carbon atoms, especially, 3, 5, 7, 9, 11, 13, 15, or 17 carbon atoms, most especially 15 carbon atoms.

In another aspect, the present invention relates to tri (alkylcarboxylato) gallium (III) products that can be represented by the formula $[RCO_2][R'CO_2][R''CO_2]Ga$, wherein R, R', and R'' are, independently, a linear or branched alkyl group having from 1 to about 26 carbon atoms, with the proviso that at least one and especially all of R, R', and R'' are not methyl.

In still a further aspect, the present invention relates to tri(alkylcarboxylato) gallium (III) compounds of formula $[RCO_2]_3Ga$, wherein R has 2 to about 26 carbon atoms, especially, 3, 5, 7, 9, 11, 13, 15, or 17 carbon atoms, most especially 15 carbon atoms.

In yet still a further embodiment, the present invention relates to tripalmitato gallium (III).

In a further aspect, the present invention relates to a method of making a tri(alkylcarboxylato) gallium (III) product comprising the step of reacting an alkyl carboxylate compound, or a mixture of alkyl carboxylate compounds, of structure $$[R\text{---}CO_2]_xM$$

wherein X is 1 or 2, R is a linear or branched alkyl group having from 2 about 26 carbon atoms, and M is selected from the group consisting of hydrogen and the alkali metals when X is 1, and the alkaline earth metals when X is 2; with a gallium salt.

In still a further aspect, the present invention relates to a method of making a tri(alkylcarboxylato) gallium (III) product comprising the step of reacting an alkyl carboxylate compound, or a mixture of alkyl carboxylate compounds, of structure

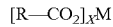
[R—CO$_2$]$_X$M wherein X is 1 or 2, R is a linear or branched alkyl group having from 1 about 26, especially 2 to about 26, carbon atoms and M is selected from the group consisting of hydrogen and the alkali metals when X is 1, and the alkaline earth metals when X is 2; with a gallium salt selected from gallium acetate, gallium nitrate, and the gallium halides. The reaction can be conducted in the presence of a solvent, especially an alkyl alcohol, for example methanol, ethanol, n-propanol, iso-propanol, n-butanol, iso-butanol, and t-butanol. The solvent can include water.

In another aspect, the present invention relates to a method of making a tri(alkylcarboxylato) gallium (III) including the steps of a) contacting a solution of an alkyl carboxylate compound (or mixture of alkyl carboxylate compounds) of structure

[R—CO$_2$]$_X$M wherein X is 1 or 2, R is a linear or branched alkyl group having from 2 to about 26 carbon atoms, and M is either an alkali metal (X is 1) or an alkaline earth metal (X is 2) in a first solvent including an alkyl alcohol, with a gallium salt or with a solution of a gallium salt in a second solvent that can include an alkyl alcohol, evaporating the resulting solution to dryness at reduced pressure, and drying the residue to constant weight to obtain the tri(alkylcarboxylato) gallium (III) product. Examples of alkyl alcohols include methanol, iso-propanol, and, especially, ethanol, to mention just a few. First and second solvents can include water. An acetate salt can be included in the reaction mixture.

In yet still another aspect, the present invention relates to a method of treating a gallium-susceptible disease or disorder such as a disease characterized by increased bone resorption, an inflammatory or autoimmune disease, or a neoplastic disease, in a mammal, especially a human, suffering from a gallium susceptible disease or disorder, comprising the step of administering to the mammal a gallium-susceptible disease-treating effective amount of a tri (alkylcarboxylato) gallium (III) product formed by the reaction of an alkyl carboxylate compound, or a mixture of alkyl carboxyalte compounds, of structure

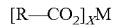
[R—CO$_2$]$_X$M wherein X is 1 or 2, R is a linear or branched alkyl group having from 1 to about 26 carbon atoms, and M is selected from the group consisting of hydrogen and the alkali metals when X is 1, and the alkaline earth metals when X is 2; with a gallium salt.

In another aspect, the present invention relates to a method of treating a disease characterized by increased bone resorption (e.g. osteoporosis, cancer-associated hypercalcemia, multiple myeloma, hyperparathyroidism, Paget's disease, and bone metastases) in a mammal comprising administering to the mammal suffering from such disease an amount of a tri(alkylcarboxylato) gallium (III) product effective to treat the disease, wherein the tri(alkylcarboxylato) gallium (III) product comprises an alkyl carboxylate substituent, R—CO$_2$, wherein R is a linear or branched alkyl group having from 1 to about 26 carbon atoms, especially 1, 2, 3, 5, 7, 9, 11, 13, 15, or 17 carbon atoms, most especially 15 carbon atoms.

In another aspect the present invention relates to a method of treating a disease characterized by increased bone resorption in a mammal (e.g. osteoporosis, cancer-associated hypercalcemia, multiple myeloma, hyperparathyroidism, Paget's disease, and bone metastases) comprising administering to the mammal suffering from such disease an amount of a tri(alkylcarboxylato) gallium (III) product effective to treat the disease, wherein the tri(alkylcarboxylato) gallium (III) product can be represented by the formula [RCO$_2$][R'CO$_2$][R"CO$_2$]Ga, wherein R, R' and R" are, independently, a linear or branched alkyl group having from 1 to about 26 carbon atoms, especially 1, 2, 3, 5, 7, 9, 11, 13, 15, or 17 carbon atoms, most especially 15 carbon atoms.

In another aspect the present invention relates to a method of treating a disease characterized by increased bone resorption in a mammal (e.g. osteoporosis, cancer-associated hypercalcemia, multiple myeloma, hyperparathyroidism, Paget's disease, and bone metastases) comprising administering to the mammal suffering from such disease an amount of a tri(alkylcarboxylato) gallium (III) product effective to treat the disease, wherein the tri(alkylcarboxylato) gallium (III) product can be represented by the formula [RCO$_2$]$_3$Ga, wherein R is a linear or branched alkyl group having from 1 to about 26 carbon atoms, especially 1, 2, 3, 5, 7, 9, 11, 13, 15, or 17 carbon atoms, most especially 15 carbon atoms.

In another aspect, the present invention relates to a method of treating an inflammatory or autoimmune disease (especially a macrophage-mediated inflammatory or autoimmune disease) in a mammal comprising the step of administering to the mammal an amount of a tri(alkylcarboxylato) gallium (III) product effective to treat the disease, wherein the tri(alkylcarboxylato) gallium (III) product comprises an alkyl carboxylate substituent, R—CO$_2$, wherein R is a linear or branched alkyl group having from 1 to about 26 carbon atoms, especially 1, 2, 3, 5, 7, 9, 11, 13, 15, or 17 carbon atoms, most especially 15 carbon atoms. Examples of gallium susceptible inflammatory or autoimmune disease include endotoxic shock, inflammatory pulmonary disease, type I diabetes, and systemic lupus erythematosus.

In another aspect, the present invention relates to method of treating an inflammatory or autoimmune disease (especially a macrophage-mediated inflammatory or autoimmune disease) in a mammal comprising the step of administering to the mammal an amount of a tri(alkylcarboxylato) gallium (III) product effective to treat the disease, wherein the tri(alkylcarboxylato) gallium (III) product can be characterized by the formula [RCO$_2$]$_3$Ga, wherein R is a linear or branched alkyl group having from 1 to about 26 carbon atoms, especially 1, 2, 3, 5, 7, 9, 11, 13, 15, or 17 carbon atoms, most especially 15 carbon atoms. Examples of gallium susceptible inflammatory or autoimmune disease include endotoxic shock, inflammatory pulmonary disease, type I diabetes, and systemic lupus erythematosus.

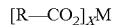
In another aspect, the present invention relates to method of treating an inflammatory or autoimmune disease (especially a macrophage-mediated inflammatory or autoimmune disease) in a mammal comprising the step of administering to the mammal an amount of a tri(alkylcarboxylato) gallium (III) product effective to treat the disease, wherein the tri(alkylcarboxylato) gallium (III) product can be characterized by the formula [RCO$_2$][R'CO$_2$][R"CO$_2$]Ga, wherein R, R' and R" are, independently, a linear or branched alkyl group having from 1 to about 26 carbon atoms, especially 1, 2, 3, 5, 7, 9, 11, 13, 15, or 17 carbon atoms, most especially 15 carbon atoms.

In another aspect, the present invention relates to a method of treating a neoplastic disease in a mammal suffering from a neoplastic disease comprising the step of administering to the mammal an amount of a tri(alkylcarboxylato) gallium (III) product effective to treat the disease, wherein the tri(alkylcarboxylato) gallium (III) product comprises an alkyl carboxylate substituent, R—$CO_2$, wherein R is a linear or branched alkyl group having from 1 to about 26 carbon atoms, especially 1, 2, 3, 5, 7, 9, 11, 13, 15, or 17 carbon atoms, most especially 15 carbon atoms. The neoplastic disease can be a hematological neoplastic disease, e.g. non-Hodgkin's lymphoma.

In another aspect, the present invention relates to a method of treating a neoplastic disease in a mammal suffering from a neoplastic disease comprising the step of administering to the mammal an amount of a tri(alkylcarboxylato) gallium (III) product effective to treat the disease, wherein the tri(alkylcarboxylato) gallium (III) product can be characterized by the formula [$RCO_2$]$_3$Ga, wherein R is a linear or branched alkyl group having from 1 to about 26 carbon atoms, especially 1, 2, 3, 5, 7, 9, 11, 13, 15, or 17 carbon atoms, most especially 15 carbon atoms. The neoplastic disease can be a hematological neoplastic disease, e.g. non-Hodgkin's lymphoma.

In another aspect, the present invention relates to a method of treating a neoplastic disease in a mammal suffering from a neoplastic disease comprising the step of administering to the mammal an amount of a tri(alkylcarboxylato) gallium (III) product effective to treat the disease, wherein the tri(alkylcarboxylato) gallium (III) product can be characterized by the formula [$RCO_2$][$R'CO_2$][$R''CO_2$]Ga, wherein R, R' and R" are, independently, a linear or branched alkyl group having from 1 to about 26 carbon atoms, especially 1, 2, 3, 5, 7, 9, 11, 13, 15, or 17 carbon atoms, most especially 15 carbon atoms.

In still yet another aspect, the present invention relates to pharmaceutical compositions, suitable for processing to solid oral dosage forms, including at least one pharmaceutically acceptable excipient and a tri(alkylcarboxylato) gallium (III) product formed by the reaction of an alkyl carboxylate compound of structure

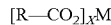

[R—$CO_2$]$_X$M wherein X is 1 or 2, R is a linear or branched alkyl group having from 1 to about 26 carbon atoms, especially 1, 2, 3, 5, 7, 9, 11, 13, 15, or 17 carbon atoms, and M is selected from the group consisting of hydrogen and the alkali metals when X is 1, and the alkaline earth metals when X is 2; with a gallium salt.

In still yet a further aspect, the present invention relates to a pharmaceutical composition comprising a tri(alkylcarboxylato) gallium (III) product having an alkyl carboxylate substituent, $RCO_2$—, wherein R is a linear or branched alkyl group having from 1 to about 26, especially 1, 2, 3, 5, 7, 9, 11, 15, or 17 carbon atoms, most especially 17 carbon atoms.

In a further embodiment, the present invention relates to a pharmaceutical composition comprising a tri(alkylcarboxylato) gallium (III) product characterized by the formula [$RCO_2$][$R'CO_2$][$R''CO_2$]Ga, wherein R, R' and R" are, independently, a linear or branched alkyl group having from 1 to about 26 carbon atoms, especially 1, 2, 3, 5, 7, 9, 11, 13, 15, or 17 carbon atoms, most especially 15 carbon atoms.

In still yet a further aspect, the present invention relates to a pharmaceutical composition comprising a tri(alkylcarboxylato) gallium (III) product characterized by the formula [$RCO_2$]$_3$Ga, wherein R is a linear or branched alkyl group having from 1 to about 26, especially 1, 2, 3, 5, 7, 9, 11, 15, or 17 carbon atoms, most especially 17 carbon atoms.

DETAILED DESCRIPTION OF THE INVENTION

As used herein in connection with a chemical compound, "CAS #" refers to the registry number assigned to that compound by the Chemical Abstracts Service.

As used herein in connection with a measured quantity, the term about indicates that variation in the measured quantity as would be expected by the skilled artisan making the measurement or determination and exercising a level of care commensurate with the objective of the measurement and the precision of the measuring apparatus being used.

As used herein, the term alkyl alcohol refers to an aliphatic alcohol having from 1 to 4 carbon atoms. Examples of alkyl alcohols include methanol, ethanol, n-propanol, iso-propanol, and the butanols, to mention just a few.

The present invention provides tri(alkycarboxylato) gallium (III) products, useful in the treatment and prophylaxis of gallium-sensitive diseases and disorders, and methods for making them. From the description below of the method of making the tri(alkylcarboxylato) gallium (III) products, the skilled artisan will recognize that the products of the present invention can include species that have other than three alkylcarboxylato moieties per gallium (III) atom and these are also contemplated by the present invention. Preferably, the tri(alkylcarboxylato) gallium (III) products can be represented by the structure: [RCO2][R'CO2][R"CO2]Ga, wherein R, R', and R" are each, independently a linear or branched alkyl group having 1 to about 26 carbon atoms, with the proviso that at least one and preferably two or more of R, R', and R" are not methyl. It will be understood that this formula is an average or nominal formula and a product represented by this formula may be made-up of a mixture of species such as [$RCO_2$][$R'CO_2$]$_2$Ga, [$R'CO_2$]$_2$[$R''CO_2$]Ga, etc.

Particularly preferred tri(alkylcarboxylato) gallium (III) products can be represented by the formula [$RCO_2$]$_3$Ga, wherein R is a linear or branched alkyl group having 2 to about 26, preferably 3, 5, 7, 9, 11, 15, or 17, carbon atoms.

The present invention further provides pharmaceutical compositions that include the tri(alkylcarboxylato) gallium (III) products and dosage forms of those pharmaceutical compositions.

The tri(alkylcarboxylato) gallium (III) products of the present invention can be characterized by, among other things, their Caco-2 cell transport values. The Caco-2 cell screening assay is well known in the art and is described in, for example, Per Artursson, et al., *Caco-2 Monolayers in Experimental and Theoretical Predictions of Drug Transport*, 46 *Advanced Drug Delivery Reviews* 27 (Elvevier 2001) and Shiyin Lee, *In Vitro Permeability Acros Caco-2 Cells (Colonic) Can Predict In Vivo (Small Intestinal) Absorption in Man—Fact or Myth*, 14 *Pharmaceutical Research*, 763 (Plenum 1997), both of which are incorporated herein by reference.

Values for Caco-2 transport are also expressed herein as transport ratios that represent the ratio of the transport rate for the proband (e.g. tri(alkylcarboxylato) gallium(III) compound) to the transport rate of a reference compound. Mannitol was the reference compound used in the calculation of the Caco-2 transport ratios discussed herein. Preferred tri(alkylcarboxylato) gallium (III) compounds have a transport ratio greater than about 3, more preferably greater than about 10.

Gallium-susceptible diseases and disorders include those that involve excessive loss of calcium from bone (i.e. excessive bone resorption) such as hypercalcimea, osteopenia, osteoporosis, hyperparathyroidism, peridontal disease, Paget's disease, as well as bone metastasis from malignant tumors. Gallium-susceptible diseases and disorders include inflammatory and autoimmune diseases, for example rheumatoid arthritis and autoimmune encephalomyelitis. Gallium compounds have also been used to intervene in the macrophage/T-cell function of the immune response and diseases or disorders in which this intervention can produce a beneficial effect are also considered within the scope of the present invention.

The tri(alkylcarboxylato) gallium (III) products of the present invention are characterized by having alkyl carboxylate substituents, $RCO_2$—, where R is a linear or branched alkyl group having 2 to about 26 carbon atoms. Preferred tri(alxylcarboxylato) gallium (III) products can be characterized by the formula: $[RCO_2]_3Ga$, wherein R is a linear or branched alkyl group having 2 to about 26 carbon atoms, especially 3, 5, 7, 9, 11, 15, or 17 carbon atoms. Tripalmitato gallium (III) (gallium tripalmitate) is a particularly preferred tri(alkylcarboxylato) gallium (III) product of the present invention.

The novel tri(alkylcarboxylato) gallium (III) products of the present invention can be made by reacting an alkyl carboxylate compound with a gallium salt. Alkyl carboxylate compounds useful in the practice of the present invention can be represented by structure I:

$$[R-CO_2]_XM \qquad (I)$$

In structure I, X is 1 or 2 and R is a linear or branched, saturated or unsaturated alkyl group having from 2 to about 26 carbon atoms. When R is a branched saturated or unsaturated alkyl group it can have, on average, up to about 3 methyl groups. When R is unsaturated, it can contain, on average, up to three loci of carbon-carbon unsaturation. Branching and unsaturation are expressed as an average number of methyl groups or an average number of unsaturation loci per "R" because, as the skilled artisan will recognize from the discussion that follows, all "R" groups in a alkyl carboxylate compound can be and typically are identical, but need not be identical.

Preferably, R is a saturated linear alkyl group having 3, 5, 7, 11, 13, or, especially, 15 or 17 carbon atoms.

When X is 1, M is hydrogen or an alkali metal. When X is 2, M is an alkaline earth metal. When M is an alkali metal or an alkaline earth metal, the alkyl carboxylate compound can be used as such or, as discussed below, it can be made in situ from the corresponding alkyl carboxylic acid.

A mixture of alkyl carboxylate compounds can also be used, e.g. a mixture of carboxylate compounds selected from $[RCO_2]_XM$, $[R'CO_2]_XM$, and $[R''CO_2]_XM$, etc., wherein R, R', R'', etc., are each, independently a linear or branched alkyl group having from 1 to about 26 carbon atoms, wherein at least one, and preferably all, of R, R', and R'' are other than methyl. Most preferably, R, R', R'' are the same and not methyl.

Essentially any gallium salt in which the gallium is in the +3 oxidation state (gallium (III)) can be used in the practice of the present invention. Preferred gallium salts include gallium (III) acetate, gallium nitrate [CAS # 69365-72-6], and gallium chloride [CAS # 13450-90-3], all of which are commercially available. The skilled artisan will recognize that the gallium salts can and often do exist as hydrates.

In one embodiment the tri(alkylcarboxylato) gallium (III) products are prepared by reacting an alkyl carboxylate compound in which M of structure I represents an alkali or alkaline earth metal with a gallium salt in the presence of a solvent that includes an alkyl alcohol. Ethanol is the preferred alkyl alcohol. The solvent can further include water. Preferably, the alkyl carboxylate compound is a sodium salt of a linear or branched, saturated or unsaturated, alkyl carboxylic acid. Sodium palmitate is a particularly preferred alkyl carboxylate compound.

The alkyl carboxylate compound (or mixture of alkyl carboxylate compounds) is combined with solvent and heated to a temperature of between about 60° C. and reflux temperature. The proportion of alkyl carboxylate compound and solvent is such that the resulting mixture is between about 1% and about 10%, preferably about 5% solids (g/mL). The alkyl carboxylate compound dissolves to an extent that is determined by, among other things, the identities of M and R, the composition of the solvent, and temperature. The gallium salt, optionally in admixture with a solvent, is combined, preferably with mechanical agitation, with the mixture of alkyl carboxylate compound and solvent to form a reaction mixture. When the gallium salt is in admixture with a solvent, the solvent includes an alkyl alcohol, preferably ethanol. The solvent can further include water. The admixture can have any concentration. Preferably the concentration is between about 15% and about 35% solids (g/mL). When water is used, it can be added with the alkyl alcohol or it can be added to the reaction mixture that results when the admixture containing the gallium salt is combined with the mixture of alkyl carboxylate compound and solvent.

The reaction mixture is heated, optionally with mechanical agitation, to a temperature of between about 50° C. and reflux temperature for about 2 to about 24 hours. Depending on, among other things, the identity of R, the solvent, the gallium salt used, and temperature, the reaction mixture can be a single phase or it can be more than one phase. If desired, the viscosity of the reaction mixture can be adjusted by addition of solvent that includes an alkyl alcohol and water, or by distilling-off solvent from the reaction mixture. Adjustment of the viscosity can facilitate collection of the product.

The tri(alkycarboxylato) gallium (III) product can be collected by, for example, suction filtration. The collected product is dried to constant weight, preferably at 50° to 70° C. under vacuum.

In another embodiment, the tri(alkycarboxylato) gallium (III) product is made by reacting an alkyl carboxylate compound that is an alkyl carboxylic acid (or mixture of alkyl carboxylic acids) with an inorganic base and a gallium salt. Inorganic bases useful in the practice of this embodiment of the present invention include alkali and alkaline earth metal oxides, hydroxides, carbonates, and bicarbonates, to mention just a few. Sodium carbonate is a preferred inorganic base.

Alkyl carboxylic acid (or acids) and inorganic base are combined in a solvent that includes an alkyl alcohol, preferably ethanol, and water (about 0,2% to about 1% water, v:v). The combination of alkyl carboxylic acid (or acids), inorganic base, and solvent is heated at a temperature of between about 60° C. and reflux, preferably at a temperature of between about 60° C. and about 65° C., until the combination thickens (about 0.5 to about 2 hours). Additional alkyl alcohol and, optionally and preferably, water are added (2:1, v:v) to adjust the viscosity. After adjustment of the viscosity, the combination is between about 0.5 and about 2% solids.

The gallium salt, optionally in admixture with a solvent that includes an alkyl alcohol, is combined, optionally with mechanical agitation, with the combination of alkyl carboxylic acid (or acids), inorganic base, and solvent. An additional portion of inorganic base can be added with or subsequent to addition of the gallium salt. The resulting mixture is heated to a temperature of between about 50° C. and reflux temperature for about 2 to about 10 hours, preferably about 3 to about 4 hours. Optionally, the viscosity of the resulting reaction mixture is adjusted by addition of solvent that includes an alkyl alcohol and, preferably, water, or by distilling-off solvent from the reaction mixture.

The tri(alkylcarboxylato) gallium (III) product is collected, for example by suction filtration, and dried to constant weight, preferably at about 50° C. to about 70° C. under vacuum.

In another embodiment, the present invention provides solid gallium-containing pharmaceutical compositions that can be processed to dosage forms for parenteral or, preferably, oral administration for treatment or prophylaxis of gallium-susceptible diseases or disorders. The pharmaceutical compositions of the invention include powders, granulates, aggregates and other solid compositions that include the novel tri(alkylcarboxylato) gallium (III) products of the present invention, or gallium triacetate. Preferred tri(alkylcarboxylato) gallium (III) compounds for preparing the pharmaceutical compositions can be represented by the formula $[RCO_2][R'CO_2][R''CO_2]Ga$, wherein R, R', and R'' are, independently, a linear or branched alkyl group having 1 to about 26, preferably 2 to about 26, most preferably 3, 5, 7, 9, 11, 15, or 17, carbon atoms.

Particularly preferred tri(alkylcarboxylato) gallium (III) compounds for use in making the pharmaceutical compositions of this embodiment can be represented by the formula $[RCO_2]_3Ga$, wherein R is a linear or branched alkyl group having 1 to about 26, preferably 2 to about 26, most preferably 3, 5, 7, 9, 11, 15, or 17, carbon atoms. In addition, the solid pharmaceutical compositions that are contemplated by the present invention can further include various excipients that the skilled artisan will know to select based on the contemplated route of administration. Excipients can include diluents, such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents like calcium carbonate and calcium diphosphate and other diluents known in the pharmaceutical art. Yet other suitable diluents include waxes, sugars and sugar alcohols like mannitol and sorbitol, acrylate polymers and copolymers, as well as pectin, dextrin and gelatin.

Further excipients that are within the contemplation of the present invention include binders, such as acacia gum, pregelatinized starch, sodium alginate, glucose and other binders used in wet and dry granulation and direct compression tableting processes. Excipients that also may be present in a solid pharmaceutical compositions of tri(alkylcarboxylato) gallium (III) products further include disintegrants like sodium starch glycolate, crospovidone, low-substituted hydroxypropyl cellulose and others. In addition, excipients may include tableting lubricants like magnesium and calcium stearate and sodium stearyl fumarate; flavorings; sweeteners; preservatives; pharmaceutically acceptable dyes and glidants such as silicon dioxide, to mention just a few.

The solid gallium-containing pharmaceutical compositions of the present invention can be processed to oral solid dosage forms such as tablets, caplets, capsules, and the like. Preferred oral solid dosage forms are formulated with a tri(alkylcarboxylato) gallium (III) product and processed to contain a unit dose of gallium for single or repeat administration. Oral solid dosage forms that include a unit dose of gallium are formulated such that a plasma level of >1 µg/mL is achieved at a steady state. Typically, an individual oral solid dosage form will have between about 0.1 wt-%% and about 20 wt-% of tri(alkylcarboxylato) gallium (III) product.

Formulation of solid pharmaceutical compositions and their processing to oral solid dosage forms is well known in the art and is described, for example, in Edward Rudnic and Joseph B. Schwarz, *Oral Solid Dosage Forms*, in 2 *Remington: The Science and Practice of Pharmacy*, 1615 (Alfonso R. Gennaro, Ed., 1995).

In another embodiment, the solid pharmaceutical composition of the present invention are processed to dosage forms for parenteral administration, including subcutaneous, intramuscular, and intravenous administration. Dosage forms for parenteral administration are formulated with an injection vehicle, for example water for injection. Pharmaceutical compositions for parenteral administration can be aqueous or oleaginous solutions, emulsions, or suspensions. Any excipients in the gallium-containing pharmaceutical composition processed to a dosage form for parenteral administration must be suitable for injection. Examples or excipients that can be used are buffers, isotonic agents, and preservatives, to mention just a few, all of which are well known in the art.

Dosage forms for parenteral administration can be supplied to the care giver as in injection-ready form, or they can be provided in the form of a dry p[powder to be reconstituted by the care giver at the time of administration.

In yet another embodiment, the present invention provides a method of treating a gallium-susceptible disease or disorder by administering to a patient, preferably a human, suffering from a gallium-susceptible disease or disorder, a gallium-susceptible disease- or disorder-treating effective amount (i.e. an amount effective to treat the disease) of a gallium-containing pharmaceutical composition that includes a tri(alkylcarboxylato) gallium (III) product of the present invention, or gallium triacetate. The pharmaceutical composition can be administered orally as an oral solid or liquid dosage form, or it can be administered parenterally. Preferably it is administered orally. Most preferably it is administered as an oral solid dosage form. For most diseases, the gallium-sensitive disease- or disorder-treating effective amount administered is such that the average blood plasma level of gallium in the patient being treated is between about 0.1 µg/mL and about 0.5 µg/mL. However, one skilled in the medical arts will know to adjust, through routine trials, the dosage depending on, among other things, the disease or disorder being treated and the characteristics of the patient (e.g. body weight).

In a preferred embodiment, the present invention provides a method of treating a mammal, especially a human, suffering from a disease characterized by increased bone resorption (e.g., osteoporosis, cancer-associated hypercalcemia, multiple myeloma, hyperparathyroidism, Paget's disease, or bone metastases), an inflammatory or autoimmune disease (e.g. endotoxic shock, inflammatory pulmonary disease, type I diabetes, or systemic lupus erythematosus), or a neoplastic disease, especially a hematological neoplastic disease, which method includes the step of administering an amount of a tri(alkylcarboxylato) gallium (III) product having an alkyl carboxylate substituent, $RCO_2$—, wherein R is a linear or branched alkyl group having from 1 to about 26 carbon atoms, preferably 1, 2, 3, 5, 7, 9, 11, 15, or 17 carbon atoms.

In a particularly preferred embodiment, the present invention provides a method of treating a mammal, especially a human, suffering from a disease characterized by increased bone resorption (e.g., osteoporosis, cancer-associated hypercalcemia, multiple myeloma, hyperparathyroidism, Paget's disease, or bone metastases), an inflammatory or autoimmune disease (e.g. endotoxic shock, inflammatory pulmonary disease, type I diabetes, or systemic lupus erythematosus), or a neoplastic disease, especially a hematological neoplastic disease, which method includes the step of administering an amount of a tri(alkylcarboxylato) gallium (III) product having the formula $[RCO_2][R'CO_2][R''CO_2]Ga$, wherein R, R', and R" are each, independently, a linear or branched alkyl group having 1 to about 26, preferably 2 to about 26, most preferably, 3, 5, 7, 9, 11, 15, or 17 carbon atoms.

Particularly preferred tri(alkylcarboxylato) gallium (III) compounds for treatment can be represented by the formula $[RCO_2]_3Ga$, wherein R is a linear or branched alkyl group having from 1 to about 26 carbon atoms, preferably 1, 2, 3, 5, 7, 9, 11, 15, or 17 carbon atoms (e.g. gallium triacetate or gallium tripalmitate).

The present invention can be further demonstrated with the following non-limiting examples.

EXAMPLE 1

Tri(octanoato) Gallium (III) Product

To a clear solution of 40.3 g of sodium caprylate in 800 mL ethanol, stirred under nitrogen at room temperature, a warm (50° C. to 65° C.) solution of 13.6 g of gallium chloride in 50 mL of ethanol was added. The resultant suspension was stirred at reflux for 2 hours, cooled to room temperature, and filtered to yield a solid. The solid was washed with ethanol and dried in a vacuum oven at 55° C. to afford 22.2 g of a solid product, tri(octanato) gallium (III) product.

EXAMPLE 2

Tri(palmitato) Gallium (III) Product

To a clear hot (50° C. to 65° C.) solution of 3.3 g of sodium palmitate in 400 mL of ethanol, a warm 50C to 65° C.) slurry of 900 mg of gallium triacetate in 125 mL of ethanol was added with stirring. The cloudy mixture became clear upon heating at reflux for 24 hours and was then filtered while hot. The filtrate was evaporated to dryness on a rotary evaporator, and the resultant residue was dried to a constant weight in an oven at 55–60° C. under vacuum to yield 2.7 g of a solid tri(palmitato) gallium (III) product.

EXAMPLE 3

Tri(palmitato) Gallium (III) Product

To a ethanolic solution of sodium palmitate prepared from palmitic acid (21.4 g, 0.0835 moles, in 175 mL ethanol) and 4.5 g of sodium carbonate at 50° C. was added an ethanolic solution of gallium(III)nitrate hydrate (111.0 g, 0.028 moles, in 50 mL ethanol). To the acidic suspension (pH=2), an additional 4.5 g portion of sodium carbonate and 1 mL of water were added. On refluxing at 78° C. for two hours the mixture acquired a pH of 9. The solids were collected by filtration and washed on the filter with 2×20 ml portions of water followed by 3×20 ml of ethanol. The filter cake was dried in a vacuum oven at 55–60° C. to constant weight. Yield, 24.2 g tri(palmitato) gallium (III) product.

EXAMPLE 4

Tri(dodecanato) Gallium (III) Product

To a mixture of 175 mL of ethanol and 25 mL of water at reflux temperature, 16.8 g of dodecanoic acid and 4.5 g of sodium carbonate was added, followed by the addition of 11.0 g of gallium nitrate nonahydrate. To the resulting suspension, 25 mL of water was added, and the mixture was stirred at reflux for two hours and then cooled to room temperature. After the addition of 100 mL of water and 100 mL of ethanol, the gel-like mixture was filtered and dried in a vacuum oven at 55–60° C. to afford 4.8 g of a solid tri(palmitato) gallium (III) product.

EXAMPLE 5

Tri(palmitato) Gallium (III) Product

To clear solution of 21.4 g of palmitic acid (83.5 m. moles) in 250 ml ethanol (SDA 3A 200) containing 1 ml water at 66–65° C., 4.5 g of sodium carbonate (42 m. moles) was added. The suspension was maintained at this temperature for 30 minutes. A very thick suspension of sodium palmitate gradually formed. Ethanol, 1250 mL and water, 150 mL water were added to the thick suspension. A solution of gallium nitrate hydrate(gallium, 14.62%; 13.4 g, 26 m. moles) in 50 ml of ethanol was added over 10 minutes. The haziness of the acidic mixture (pH=2) increased and stabilized. Another 4.5 g portion of sodium carbonate (42 m. moles) was added and the mixture was refluxed for 4 hr. The gel-like voluminous white material was collected by filtration using a 18.5 mm diameter buchner funnel using 100 mm vacuum. The material was drawn dry using a plastic damper. The wet product (49.6 g) was dried in a oven at full vacuum and 55–65° C. to constant weight {Yield, 18.9 g tri(palmitato) gallium (III) product}.

EXAMPLE 6

Tri(palmitato) Gallium (III) Product

To a clear ethanolic solution of palmitic acid (21.4 g in 350 ml, 83.5 m. moles) containing 1 ml of water, $Na_2CO_3$ (4.5 g, 42.5 m. moles) was added. The mixture was maintained at 60–65° C. for 1 hour during which time it thickened gradually. Ethanol, 1250 ml, and water, 625 ml of water were added. A clear solution at 65° C. was obtained. Alcoholic Ga(NO3)$_3$hydrate (13.4 g in 50 ml 14.62% Ga, 28 m. moles) was added over 10 minutes. The hazy mixture was refluxed at 78–80° C. for 3 hours. The pH of the reaction mixture was 3. The mixture was concentrated to ca. 400 ml to obtain flaky looking solids. The solids were collected by vacuum filtration and successively washed with 50 ml, 75 ml and 3×100 ml portions of water. The product was sucked dry by using Gast pump at 27" vacuum. The final drying of the material to weight was done in a vacuum oven at 55–60° C./full vacuum. Yield, 21.6 g tri(palmitato) gallium (III) product.

EXAMPLE 7

Tri(palmitato) Gallium (III) Product

To 400 ml ethanol (SDA 3A 200) containing 50 ml water and 21.4 g of palmitic acid (83.5 m. moles) at 60–65° C., 4.5 g of solid $Na_2CO_3$ (42.5 m. moles) was added. The mixture was held at 60–65° C. for 1 hour. Ethanol. 1100 ml, and water, 700 ml, were added. The clear solution was kept at 60–65° C. for one hour. A solution of 13.4 g of $Ga(NO_3)_3$ hydrate {Ga, 14.62%; 28 m. moles} in 50 ml ethanol was then added over 15 minutes. The mixture became hazy and was maintained at 60–65° C. for 2 hours. An additional 4.5 g of solid $Na_2CO_3$ (42.5 m. moles) was added and the mixture was refluxed for 3 hours. On cooling to room temperature a gel formed. The gel was filtered, drawn dry with vacuum, and dried to constant weight in a vacuum oven at 60–65° C./full vacuum. Yield, 9.7 g tri(palmitato) gallium (III) product. The filtrate (pH >8) on leaving aside deposited more gel like material.

EXAMPLE 8

Caco-2 Test Protocols

The evaluation protocol of the apical to basolateral (A to B) absorption of a test article in Caco-2 monolayer cells is known to those of skill in the art as follows.

Caco-2 cells are plated in individual Transwells® in 24-well tissue culture plates and cultured for 3 days to establish the cultures. After 3 days, the cells are tested for transepithelial electrical resistance (TEER) as a measure of the formation of tight junctions between cells. Only cells with a TEER equal to or greater than about 330 $\Omega \cdot cm^2$ $cm^2$ are used. The proband or the control article (reference) is applied to the apical side of Caco-2 cells and incubated for 2 hours (37° C., 5% $CO_2$). At t=2 hr, the media in each well are collected and stored until later analysis. Aliquots of the dosing solution are retained for analysis along with the samples.

The concentrations of the test and control articles are typically in the range from about 0.01 μg/mL to about 10 μg/mL; preferably in the range of about 1.0 μg/mL to about 5.0 μg/mL. For test samples, the analysis is repeated three times while the N value for all the control groups is six. The controls are [$^3$H]propranolol for fast transport and [$^3$H] mannitol for slow transport.

The gallium product proband and dosing solution samples are analyzed by inductive coupled plasma optical emission spectrometry (ICP-OCP) to measure gallium concentration. Any non-gallium test articles and dosing solution samples are analyzed by HPLC. Positive controls are analyzed using scintillation counting.

Table 1 contains the Caco-2 testing results for the thee gallium-containing compounds synthesized above, along with references, gallium maltolate and gallium nitrate, and controls, propranalol and mannitol.

TABLE 1

| Example | Description | % Absorbed | Trsp nm/sec | Ratio | Comments |
|---|---|---|---|---|---|
|  | Propranalol | 24.118 | 104.679 | 9.3 | Positive control |
|  | Mannitol | 2.603 | 11.298 | 1 | Negative control |
| 1 | Gallium Trioctanoate Product | 9.890 | 42.930 | 3.8 |  |
| 2 | Gallium Tripalmitate Product | 72.000 | 312.500 | 27.7 |  |
| 3 | Gallium Tridodecanoate Product | 31.579 | 137.060 | 12.1 |  |
|  | Gallium Maltolate | 24.793 | 107.610 | 9.5 | Reference |
|  | Gallium Nitrate | 13.740 | 59.640 | 5.3 | Reference |

We claim:

1. A tri(alkylcarboxylato) gallium (III) product formed by the reaction of at least one alkyl carboxylate compound of structure $$[R-CO_2]_X M$$

wherein R is a linear or branched alkyl group having from 2 to about 26 carbon atoms and M is selected from the group consisting of hydrogen and the alkali metals when X is 1, and the alkaline earth metals when X is 2; with a gallium salt.

2. The tri(alkylcarboxylato) gallium (III) product of claim 1 wherein the gallium salt is selected from the group consisting of gallium acetate, gallium nitrate, and the gallium halides.

3. The tri(alkylcarboxylato) gallium (III) product of claim 2 wherein, when M is hydrogen, the reaction is carried out in the presence of an inorganic base.

4. The tri(alkylcarboxylato) gallium III product of claim 3 wherein the inorganic base is an alkali metal carbonate or bicarbonate, an alkaline earth metal carbonate or bicarbonate, or an alkali metal hydroxide.

5. The tri(alkylcarboxylato) gallium (III) product of claim 1 wherein R has from 3 to about 17 carbon atoms.

6. The tri(alkylcarboxylato) gallium (III) product of claim 5 wherein R is a linear or branched alkyl group having 3, 5, 7, 11, 13, 15, or 17 carbon atoms.

7. The tri(alkycarboxalato) gallium (III) product of claim 6 wherein R has 15 carbon atoms.

8. The product of claim 1 wherein the reaction is carried out in the presence of a solvent that comprises an <<alkyl alcohol>> selected from the group consisting of methanol, ethanol, n-propanol, iso-propanol, 2-butanol, t-butanol, and iso-butanol.

9. The tri(alkycarboxalato) gallium (III) product of claim 8 wherein the solvent further comprises water.

10. The tri(alkylcarboxylato) gallium (III) product of claim 9 wherein the reaction is carried out in refluxing solvent comprising an alkyl alcohol and water at pH equal to or greater that about 8.

11. A tri(alkylcarboxylato) gallium (III) product of formula $$[RCO_2][R'CO_2][R''CO_2]Ga,$$

wherein R, R', and R" are each, independently, a linear or branched alkyl group having from 1 to about 26 carbon atoms, with the proviso that at least one of R, R', and R" is other than methyl.

12. The tri(alkylcarboxylato) gallium (III) product of claim 11 wherein R, R', and R" each have, independently, 1, 2, 3, 5, 7, 11, 15, or 17 carbon atoms.

13. A tri(alkylcarboxylato) gallium (III) product of formula

[RCO$_2$]$_3$Ga wherein R is a linear or branched alkyl group having from 2 to about 26 carbon atoms.

14. The tri(alkylcarboxylato) gallium (III) product of claim 13 wherein R has 2, 5, 7, 11, 15, or 17 carbon atoms.

15. Tripalmitato gallium (III).

16. A method of making a tri(alkylcarboxylato) gallium (III) product comprising the step of reacting at least one alkyl carboxylate compound of structure

[R—CO$_2$]$_x$M wherein R is a linear or branched alkyl group having from 2 to about 26 carbon atoms and M is selected from the group consisting of hydrogen and the alkali metals when X is 1, and the alkaline earth metals when X is 2; with a gallium salt.

17. The method of claim 16 wherein the gallium salt is selected from the group consisting of gallium acetate, gallium nitrate, and the gallium halides.

18. The method of claim 16 wherein the alkyl carboxylate compound is initially in solution.

19. The method of claim 16 wherein the reacting is carried-out in the presence of a solvent that comprises an alkyl alcohol, wherein the alkyl alcohol is selected from the group consisting of methanol, ethanol, n-propanol, iso-propanol, 2-butanol, t-butanol, and iso-butanol.

20. The method of claim 19 wherein the alkyl alcohol is ethanol.

21. The method of claim 19 wherein the solvent further comprises water.

22. The method of claim 16 wherein the at least one alkyl carboxylate compound comprises a mixture of two or more alkyl carboxylate compounds selected from [RCO$_2$]$_x$M, [R'CO$_2$]$_x$M, and [R"CO$_2$]$_x$M, wherein R, R', and R" are, independently, a linear or branched alkyl group having from 2 to about 26 carbon atoms, with the proviso that the mixture includes at least two different alkyl carboxylate compounds.

23. A method of making a tri(alkylcarboxylato) gallium (III) product comprising the steps of:
  a) contacting a solution of at least one alkyl carboxylate compound of structure

[R—CO$_2$]$_x$M wherein R is a linear or branched alkyl group having from 2 to about 26 carbon atoms and M is either an alkali metal when X is 1 or an alkaline earth metal when X is 2 in a first solvent comprising an alkyl alcohol, with a gallium salt or with a solution of a gallium salt in a second solvent comprising an alkyl alcohol,
  b) evaporating the resulting solution to dryness at reduced pressure, and
  c) drying the residue to constant weight to obtain the tri(alkylcarboxylato) gallium (III) product.

24. The method of claim 23 wherein the at least one alkyl carboxylate compound comprises a mixture of two or more alkyl carboxylate compounds selected from [RCO$_2$]$_x$M, [R'CO$_2$]$_x$M, and [R"CO$_2$]$_x$M, wherein R, R', and R" are, independently, a linear or branched alkyl group having from 2 to about 26 carbon atoms, with the proviso that the mixture includes at least two different alkyl carboxylate compounds.

25. The method of claim 23 wherein the alkyl alcohol of the first and second solvents is ethanol.

26. The method of claim 23 wherein the first and second solvents further comprise water.

27. The method of claim 23 wherein the alkyl carboxylate compound of step (a) is prepared by reacting at least one alkyl carboxylic acid with an inorganic base in the presence of a solvent that comprises an alkyl alcohol.

28. The method of claim 27 wherein the solvent in the presence of which the alkyl carboxylate compound is prepared further comprises water.

29. The method of claim 28 wherein the solvent in the presence of which the alkyl carboxylate compound is prepared consists essentially of ethanol and water.

30. The method of claim 27 wherein the inorganic base is selected from the group consisting of the alkali metal carbonates and the alkaline earth metal carbonates.

31. A pharmaceutical composition comprising a tri(alkylcarboxylato) gallium (III) product of formula

[RCO$_2$][R'CO$_2$][R"CO$_2$]Ga wherein R, R', and R" are each, independently, a linear or branched alkyl group having from 1 to about 26 carbon atoms, and at least one pharmaceutically acceptable excipient.

32. The pharmaceutical composition of claim 31 wherein R, R', and R" each have, independently, 2, 3, 5, 7, 11, 15, or 17 carbon atoms.

33. The pharmaceutical composition of claim 31 wherein the tri(alkylcarboxylato) gallium (III) compound can be represented by the formula

[RCO$_2$]$_3$Ga wherein R is a linear or branched alkyl group having 1 to about 26 carbon atoms, and at least one pharmaceutically acceptable excipient.

34. A pharmaceutical composition comprising a tri(alkylcarboxylato) gallium (III) product formed by the reaction of at least one alkyl carboxylate compound of structure

[R—CO$_2$]$_x$M wherein R is a linear or branched alkyl having from 2 to about 26 carbon atoms and M is selected from the group consisting of hydrogen and the alkali metals when X is 1, and the alkaline earth metals when X is 2; with a gallium salt, and at least one pharmaceutically acceptable excipient.

35. A method of treating a disease characterized by increased bone resorption in a mammal comprising administering to the mammal suffering from such disease an amount of a tri(alkylcarboxylato) gallium (III) product effective to treat the disease, wherein the tri(alkylcarboxylato) gallium (III) product can be represented by the formula

[RCO$_2$][R'CO$_2$][R"CO$_3$]Ga wherein R, R', and R" are each, independently a linear or branched alkyl group having from 1 to about 26 carbon atoms.

36. The method of claim 35 wherein the tri(alkylcarboxylato) gallium (III) product can be represented by the formula

[RCO$_2$]$_3$Ga wherein R is a linear or branched alkyl group having 1 to about 26 carbon atoms.

37. The method of claim 35 wherein the disease characterized by increased bone resorption is selected from the group consisting of osteoporosis, cancer-associated hypercalcemia, multiple myeloma, hyperparathyroidism, Paget's disease, and bone metastases.

38. The method of claim 34 wherein the mammal is a human.

39. A method of treating a disease characterized by increased bone resorption, in a mammal suffering from such disease comprising the step of administering to the mammal an amount of a <<tri(alkylcarboxylato) gallium (III) product>> effective to treat such disease, wherein the tri(alkylcarboxylato) gallium (III) compound is formed by the reaction of at least one alkyl carboxylate compound of structure

[R—CO₂]ₓM wherein R is a linear or branched alkyl group having from 2 to about 26 carbon atoms and M is selected from the group consisting of hydrogen and the alkali metals when X is 1, and the alkaline earth metals when X is 2; with a gallium salt,
wherein the disease is selected from the group consisting of osteoporosis, cancer-associated hypercalcemia, multiple myeloma, hyperparathyroidism, Paget's disease, and bone metastases.

40. The method of claim 39 wherein the mammal is a human.

41. A method of treating an inflammatory or autoimmune disease in a mammal comprising the step of administering to the mammal an amount of a tri(alkylcarboxylato) gallium (III) compound effective to treat the disease, wherein the tri(alkylcarboxylato) gallium (III) compound can be represented by the formula

[RCO₂][R'CO₂][R"CO₃]Ga wherein R, R', and R" are each, independently a linear or branched alkyl group having from 1 to about 26 carbon atoms.

42. The method of claim 41 wherein the tri(alkylcarboxylato) gallium (III) compound can be represented by the formula

[RCO₂]₃Ga, wherein R is a linear or branched alkyl group having from 1 to about 26 carbon atoms.

43. The method of claim 41 wherein the inflammatory or autoimmune disease is a macrophage-mediated inflammatory or autoimmune disease.

44. The method of claim 43 wherein the inflammatory or autoimmune disease is selected from the group consisting of endotoxic shock, inflammatory pulmonary disease, type I diabetes, and systemic lupus erythematosus.

45. The method of claim 41 wherein the mammal is a human.

46. A method of treating an inflammatory or autoimmune disease in a mammal suffering from such disease comprising the step of administering to the mammal an amount of a tri(alkylcarboxylato) gallium (III) product effective to treat the disease wherein the tri(alkylcarboxylato) gallium (III) product is formed by the reaction of at least one alkyl carboxylate compound of structure

[R—CO₂]ₓM wherein R is a linear or branched <<alkyl group>> having from 2 to about 25 carbon atoms and M is selected from the group consisting of hydrogen and the alkali metals when X is 1, and the alkaline earth metals when X is 2; with a gallium salt.

47. The method of claim 46 wherein the inflammatory or autoimmune disease is a macrophage mediated autoimmune disease.

48. The method of claim 47 wherein the inflammatory or autoimmune disease is selected from the group consisting of endotoxic shock, inflammatory pulmonary disease, type I diabetes, and systemic lupus erythematosus.

49. The method of claim 46 wherein the mammal is a human.

50. A method of treating a neoplastic disease in a mammal suffering from a neoplastic disease comprising the step of administering to the mammal an amount of a tri(alkylcarboxylato) gallium (III) product effective to treat the disease, wherein the tri(alkylcarboxylato) gallium (III) product can be represented by the formula

[RCO₂][R'CO₂][R"CO₃]Ga wherein R, R', and R" are each, independently, a linear or branched alkyl group having from 1 to about 26 carbon atoms.

51. The method of claim 50, wherein the tri(alkylcarboxylato) gallium (III) product can be represented by the formula

[RCO₂]₃Ga, wherein R is a linear or branched alkyl group having from 1 to about 26 carbon atoms.

52. The method of claim 50 wherein the neoplastic disease is a hematological neoplastic disease.

53. The method of claim 52 wherein the neoplastic disease is non-Hodgkin's lymphoma.

54. The method of claim 50 wherein the mammal is a human.

55. A method of treating a neoplastic disease in a mammal suffering from a neoplastic disease comprising the step of administering to the mammal a neoplastic disease-treating effective amount of a tri(alkylcarboxylato) gallium (III) product formed by the reaction of at least one alkyl carboxylate compound of structure

[R—CO₂]ₓM wherein R is a linear or branched alkyl group having from 2 to about 25 carbon atoms and M is selected from the group consisting of hydrogen and the alkali metals when X is 1, and the alkaline earth metals when X is 2; with a gallium salt.

56. The method of claim 55 wherein the neoplastic disease is a hematological disease.

57. The method of claim 55 wherein the neoplastic disaease non-Hodgkin's lymphoma.

58. The method of claim 55 wherein the mammal is a human.

* * * * *

UNITED STATES PATENT AND TRADEMARK OFFICE
CERTIFICATE OF CORRECTION

PATENT NO. : 7,119,217 B2
APPLICATION NO. : 10/668473
DATED : October 10, 2006
INVENTOR(S) : Jack B. Jiang It is certified that error appears in the above-identified patent and that said Letters Patent is hereby corrected as shown below:

On the title page, item [56] under Other Publications:

line 13, change "response" to -- reports --;

line 35, change " Vol.80, No.8" to -- Vol. 80, No. 58 --;

line 39, change "Dec. 1990" to -- Dec. 1, 1990 --;

On the title page, item [56] Page 2, Column 1, line 4, change " No. 6 (1999) to -- Vol. 6, No. 6, (Nov. 1999) --;

On the title page, item [56] Page 2, Column 2, line 3, change " Vol. 46 (2001)" to -- Vol. 46, Nos.1-3, (March 1, 2001) --.

On the title page, item [56] Page 2, Column 2, line 6, change "(1997)" to -- (June 1997) --;

On the title page, item [56] Page 2, Column 2, line 9, change "1995" to -- Mack Pub. Co. 1995 --;

Column 1, line 26, change "Vol. 68, 1971" to -- Vol. 68(7), July 1971 --;

Column 1, line 34, change "Vol. 71, 1987" to -- Vol. 71(1), Jan. 1987 --;

Column 1, line 46, change "Vol. 80, 1997" to -- Vol. 80(58), Oct. 15, 1997 --;

Column 1, line 50, change "Vol.113, 1990" to -- Vol. 113(11), Dec. 1, 1990 --;

Column 3, line 62, change "alky" to -- alkyl --;

Column 9, line 7, change "hypercalcimea" to -- hypercalcemia --;

Column 10, line 61, change "0,2%" to -- 0.2% --;

Column 11, line 2, change "0.5 and" to -- 0.5% and --;

Column 12, line 12, change "0.1wt-%%" to -- 0.1wt-% --;

UNITED STATES PATENT AND TRADEMARK OFFICE
CERTIFICATE OF CORRECTION

PATENT NO. : 7,119,217 B2
APPLICATION NO. : 10/668473
DATED : October 10, 2006
INVENTOR(S) : Jack B. Jiang It is certified that error appears in the above-identified patent and that said Letters Patent is hereby corrected as shown below:

Column 12, line 36, change "p[powder" to -- powder --;

Column 13, line 51, change "50C to 65° C." to -- 50° C. 65°C. --;

Column 13, line 67, change "111.0g" to -- 11.0g --;

Column 14, line 30, change "66-65° C." to -- 60-65° --;

Column 14, line 55, change "and water, 625 ml of water" to -- and 625 ml of water --;

Column 14, line 57, change "Ga(NO3)$_3$ hydrate" to -- Ga(NO$_3$)$_3$ hydrate --;

Column 15, line 51, change "$\Omega.cm^2\ cm^2$" to -- $\Omega.cm^2$ --;

Column 15, line 67, change "(ICP-OCP)" to -- (ICP-OES) --;

Column 16, line 4, change "thee" to -- three --;

Column 16, line 64, change "greater that" to -- greater than --;

Column 19, line 6, change "claim 34" to -- claim 35 --;

Column 19, line 11, change "prod-uct" to -- product --;

Signed and Sealed this

Twenty-second Day of September, 2009

David J. Kappos
*Director of the United States Patent and Trademark Office*